United States Patent [19]

Rapaport

[11] Patent Number: 5,049,372

[45] Date of Patent: * Sep. 17, 1991

[54] ANTICANCER ACTIVITIES IN A HOST BY INCREASING BLOOD AND PLASMA ADENOSINE 5'-TRIPHOSPHATE (ATP) LEVELS

[76] Inventor: Eliezer Rapaport, 6 Whittier Pl., Apartment 8-J, Boston, Mass. 02114

[*] Notice: The portion of the term of this patent subsequent to Nov. 14, 2006 has been disclaimed.

[21] Appl. No.: 223,503

[22] Filed: Jul. 25, 1988

Related U.S. Application Data

[63] Continuation-in-part of Ser. No. 397,897, Jul. 13, 1982, Pat. No. 4,880,918.

[51] Int. Cl.$^5$ .................. A61K 31/70; C07H 19/16
[52] U.S. Cl. .................................. 424/1.1; 536/27; 514/47
[58] Field of Search ............... 514/47; 424/1.1; 536/27

[56] References Cited

U.S. PATENT DOCUMENTS

| | | | |
|---|---|---|---|
| 4,141,972 | 2/1979 | Nishino et al. | 514/47 |
| 4,880,918 | 11/1989 | Rapaport | 536/27 |

FOREIGN PATENT DOCUMENTS

| | | | |
|---|---|---|---|
| 0100022 | 2/1984 | European Pat. Off. | 424/1.1 |
| 0053897 | 4/1977 | Japan | 514/47 |
| 0040635 | 3/1980 | Japan | 514/47 |
| 56-34697 | 4/1981 | Japan | |

OTHER PUBLICATIONS

Rapaport et al., "Anticancer Activities of Adenine Nucleotides . . . ", *Proceeding of Nat. Acad. of Science, U.S.A.,* May, 1988.

Chemical Abstracts 98:119267F.

Elmaleh, et al., "$^{99m}$Tc-Labelled Nucleotides as Tumor-Seeking Radio Diagnostic Agents", in Proc. Natl. Acad. Sci. U.S.A., vol. 81, pp. 918–921 (Feb. 1984).

Chahwala, et al., "Extracellular ATP Induces Ion Fluxes and Inhibits Growth of Friend Erythroleukemia Cells", *Journal of Biological Chemistry,* vol. 259, No. 22 (Nov. 25, 1984), pp. 13717–13722.

Kerr, et al., "Proc. Natl. acad. Sci.", U.S.A., vol. 75, No. 1, pp. 256–260, Jan. 1978, pppA2'p5'A2'p5'A.

*Primary Examiner*—John S. Maples
*Attorney, Agent, or Firm*—Pollock, Vande Sande & Priddy

[57] ABSTRACT

Growth of tumor cells in a host is arrested by the generation of elevated blood and plasma levels of adenosine 5'-triphosphate in said host. These elevated levels can be achieved, for instance, by administering adenosine 5'-monophosphate, adenosine 5'-triphosphate, pharmaceutically acceptable salts thereof, or chelates thereof, or radio-nuclides thereof. Weight loss caused by cancer cachexia is substantially inhibited.

45 Claims, 3 Drawing Sheets

ANTICANCER ACTIVITIES IN A HOST BY INCREASING BLOOD AND PLASMA ADENOSINE 5'-TRIPHOSPHATE (ATP) LEVELS

CROSS-REFERENCE TO RELATED APPLICATIONS

This is a continuation-in-part of my co-pending application Ser. No. 06/397,897 filed July 13, 1982 now U.S. Pat. No. 4,880,918 and entitled "Arrest and Killing of Tumor Cells by Adenosine 5'-Diphosphate and Adenosine 5'-Triphosphate."

DESCRIPTION

1. Technical Field

The present invention is concerned with the selective inhibition of the growth and subsequent killing of tumor cells in a host (e.g., human tumor cells) by increasing the blood and plasma adenosine 5'- triphosphate (ATP) levels in the host. The elevated blood and plasma ATP levels can be achieved, for example, by administering adenosine 5'-monophosphate, adenosine 5'-triphosphate, pharmaceutically acceptable salts thereof; or chelates thereof; or radio-nuclides thereof. The treatment according to the present invention is also of a host afflicted with tumors to the extent that tissues or organ functions of the host are adversely effected. This treatment substantially inhibits host weight losses which are caused by cancer cachexia.

2. Background Art

It is known to use antimetabolites (e.g., cytotoxic nucleosides or bases) such as purines and pyrimidines as antineoplastic drugs. However, such antimetabolites are taken up by both normal and tumor cells and, therefore, not only can inhibit the growth of tumor cells, but also adversely affect normal cells in the host.

U.S. Pat. No. 4,291,024 to Turcotte suggests a process for the preparation of liponucleotide analogs of nucleosides or bases having known cytotoxic activity (e.g., 1-β-D-arabinofuranosyl-cytosine, known as Ara-C). This patent suggests that these liponucleotide analogs of nucleosides provide a means for delivering cytotoxic nucleosides into the tumor cells. Once inside the cells, the cytotoxic nucleoside can be released in a phosphorylated form, thus circumventing the dependency upon kinase activity on the nucleoside itself. This is beneficial since the cytotoxic nucleosides or bases exert their anti-proliferative activities via the nucleoside triphosphate form. The objects stated in U.S. Pat. No. 4,291,024 do not specifically mention delivery of normal cellular metabolites (e.g., AMP, ADP, or ATP) into tumor cells via the liponucleotide analog. The liponucleotide analog reported by Turcotte enter the cancer cell via the process of lysosomo-tropism or related membrane phenomena; as such, these analogs can also enter normal non-cancerous cells (e.g., bone marrow, lymph node, or intestinal epithelium cells), resulting in disruption of the normal cycling cell metabolism.

ATP is a known vasodilator that may cause circulatory changes in humans and experimental animals. See Davies, et al., "Circulatory and Respiratory Effects of Adenosine Triphosphate in Man" in *Circulation* 3:543–550 (April 1951); Duff, et al., "A Quantitative Study of the Response to Adenosine Triphosphate of the Blood Vessels of the Human Hand and Forearm" in *J. Physiol.* 125:581–589 (1954); Rowe, et al., "The Systemic and Coronary Hemodynamic Effects of Adenosine Triphosphate and Adenosine" in *American Heart J.* 64:228–234 (1962). Moreover, cellular pools of acid-soluble nucleotides, especially ADP and ATP, have been previously shown by Rapaport and collaborators to act in the regulation of DNA replication and growth of mammalian cells. See Rapaport, et al., "Incorporation of Adenosine into ATP:Formation of Compartmentalized ATP" in *Proc. Natl. Acad. Sci. USA*, Vol. 73, No. 9:3122–3125 (September 1976); Rapaport, et al., "Increased Incorporation of Adenosine into Adenine Nucleotide Pools in Serum-Deprived Mammalian Cells" in *Proc. Natl. Acad. Sci. USA*, Vol. 75, No. 3:1145–1147 (March 1978); Rapaport, et al., "Elevated Nuclear ATP Pools and ATP/ADP Ratios Mediate Adenosine Toxicity in Fibroblasts" in *Regulation of Macromolecular Synthesis by Low Molecular Weight Mediators*, Academic Press, 1979, pp. 223–231; Rapaport, et al., "Regulation of DNA Replication in S Phase Nuclei by ATP and ADP Pools" in *Proc. Natl. Acad. Sci. USA*, Vol. 76, No. 4:1643–1647 (April 1979); Rapaport, et al., "Selective High Metabolic Lability of Uridine, Guanosine and Cytosine Triphosphates in Response to Glucose Deprivation and Refeeding of Untransformed and Polyoma Virus-transformed Hamster Fibroblasts" in *J. Cell. Physiol.*, Vol. 101, No. 2:229–236 (November 1979); Rapaport, et al., "Selective High Metabolic Lability of Uridine Triphosphate in Response to Glucosamine Feeding of Untransformed and Polyoma Virus-transformed Hamster Fibroblasts" in *J. Cell. Physiol.*, 104:253–259 (1980); Rapaport, "Compartmentalized ATP Pools Produced from Adenosine Are Nuclear Pools" in *J. Cell. Physiol.*, 105:267–274 (1980); and Rapaport, et al., "Retinoic Acid-Promoted Expansion of Total Cellular ATP Pools in 3T3 Cells Can Mediate its Stimulatory and Growth Inhibitory Effects" in *J. Cell. Physiol.*, 110:318–322 (1982).

However, these references showing use of ADP and ATP as regulators of DNA replication and growth of mammalian cells do not disclose that the materials, or a process of using such materials, selectively attack tumor cells (e.g., human tumor cells) and do not attack normal cells, leading to the arrest of growth and killing of said tumor cells while causing substantially no arrest of growth or killing of normal cells.

More recently, it has been disclosed in my copending U.S. patent application Ser. No. 397,897 filed on July 13, 1982, now U.S. Pat. No. 4,880,918 disclosure of which is incorporated herein by reference and my corresponding European patent application No. 83106808.5 and now European Patent 0100022 that exposure of a variety of tumor cells (e.g., a variety of types of human tumor cells) to low doses of ADP and/or ATP will result in marked inhibition of DNA synthesis and arrest of significant populations of cells in the S phase of their cycle, and continued exposure to such low doses of ADP and/or ATP will result in death of such tumor cells with such effect on tumor cells occurring with substantially no effect on normal cells. However, the in vitro tests carried out therein suggested that adenosine 5'-monophosphate (AMP) would not inhibit cellular growth. Also, said disclosure does not specifically recognize the mechanism of arresting growth of tumor cells by generating elevated blood and plasma ATP levels in the tumor-bearing host.

The invention disclosed in U.S. patent application Ser. No. 397,897, now U.S. Pat. No. 4,880,819 to Rapaport, and in the corresponding European application No. 83106808.5, now European Patent 0100022 represents the initial and basic art for the use of adenosine 5'-triphosphate (ATP) and adenosine 5'-diphosphate (ADP) against tumors. The two scientific papers outlining the experimental results disclosed in the above-mentioned application were published in highly reputable scientific journals (Rapaport, E., "Treatment of Human Tumor Cells with ADP or ATP Yields Arrest of Growth in the S Phase of the Cell Cycle", *J. Cellular Physiol.*, 114, 279–283, 1983; Rapaport, E., et al., "Growth Inhibition of Human Tumor Cells in Soft-Agar Cultures by Treatment with Low Levels of Adenosine 5'-Triphosphate", *Cancer Research*, 43, 4402–4406, 1983). These two papers are cited by others in the scientific literature as the first demonstration of the growth-inhibiting activities of extracellular ATP or ADP against animal or human tumor cells in in vitro systems that are commonly used to predict the sensitivity of human tumors to chemotherapeutic agents.

Summary of Invention

The present application discloses, for the first time, generating extracellular ATP levels in the blood of tumor-bearing hosts. These extracellular (blood plasma compartment) levels of ATP act against the tumors and the present invention also identifies the methods and mechanisms of obtaining elevated blood (cellular) and plasma (extracellular) ATP levels. These ATP pools were demonstrated to possess substantial anticancer activities in murine (mouse) models. These models are commonly used for the assessment of the therapeutic efficacy and toxicity towards a host of cancer chemotherapeutic agents. Both the previous U.S. and European applications by Rapaport, as well as any scientific publication by myself or others do not discuss 1) generating extracellular (blood plasma) ATP pools from red blood cell (RBC) ATP pools and the ability of these ATP pools to substantially inhibit tumor growth in a host, 2) the administration of AMP to a tumor-bearing host for the purpose of expanding red blood cell ATP pools, and 3) the use of AMP and/or ATP for the inhibition of the adverse effects of cancer cachexia in tumor-bearing hosts.

Cancer associated cachexia results in severe anatomical alterations that originate in the interrelationship between the tumor and host tissues, organs, and their functions. One of the most profound conditions exhibited in tumor-bearing hosts is host tissue depletion which leads to a rapid weight loss (for a review see Costa, G., "Cachexia, The Metabolic Component of Neoplastic Diseases", *Cancer Research*, 37, 2327–2335, 1977). To date, total parenteral nutrition or the anabolic hormone insulin were shown to be effective against rapid weight losses in tumor-bearing hosts (Moley, J. F., et al., "Body Composition Changes in Rats with Experimental Cancer Cachexia: Improvement with Exogenous Insulin", *Cancer Research*, 48, 2784–2787, 1988). Both of these treatments, however, do not inhibit the growth of the tumor itself with indications that total parenteral nutrition actually increases tumor growth (Popp, M. B., et al., "Host and Tumor Responses to Increasing Levels of Intravenous Nutritional Support", *Surgery*, 94, 300–308, 1983).

The present application provides the initial disclosure of a mechanism for inhibiting cancer cachexia in tumor-bearing hosts. In contrast to the present art, the administration of AMP and/or ATP into tumor-bearing hosts result not only in the inhibition of host weight loss, but also act in inhibiting the growth of the tumor. Experimental evidence presented in this disclosure shows that the inhibition of host weight loss in tumor-bearing hosts (which is the most severe outcome of cancer cachexia) and the inhibition of tumor growth by administration of AMP and/or ATP are two separate consequences of this treatment and are not dependent or related to each other. Namely, the inhibition of host weight loss in tumor-bearing hosts is not simply the result of the inhibition of tumor growth after administration of AMP or ATP. Both phenomena (inhibition of weight loss in tumor-bearing hosts and inhibition of tumor growth), however, originate with the same physiological mechanism, the expansion of blood (total cellular), and blood plasma (extracellular) ATP levels.

The present invention is concerned with selectively arresting the growth of and the killing of tumor cells in a host (e.g., human tumor cells). The present invention comprises administering to a host having tumor cells (a tumor-bearing host), adenosine 5'-monophosphate (AMP), or pharmaceutically acceptable salts thereof, or chelates thereof, or radio-nuclides thereof in an amount sufficient to increase the blood and plasma levels of adenosine 5'-triphosphate (ATP) in the host to a sufficient extent to thereby arrest the growth of and kill tumor cells.

A further aspect of the present invention is concerned with treating a host afflicted with a tumor where the affliction or disease has progressed to an advanced stage whereby there has been a profound deterioration in host tissues or organ functions. This aspect of the present invention arrests the growth of tumor cells in such a host and while substantially inhibiting weight loss caused by cancer cachexia in the host. The treatment involves increasing the blood and plasma ATP levels of the host to a level sufficient to thereby arrest the growth of the tumor and while substantially inhibiting weight loss caused by cancer cachexia.

Discussion concerning the scientific basis of the present invention can be found in two papers which are to be published, disclosures of which are incorporated herein by reference. One copy of each is being filed along with this application. The two papers are Rapaport, E., "Experimental Cancer Therapy in Mice by Adenine Nucleotides", *European Journal of Cancer & Clinical Oncology*, 24 1491–1497, 1988; and Rapaport, E. and Fontaine, J., "Anticancer Activities of Adenine Nucleotides in Mice are Mediated Through Expansion of Erythrocyte ATP Pools", *Proceedings of the National Academy of Sciences USA*, 86, 1662–1666, 1989. These papers clearly demonstrate that the three basic aspects of this disclosure do not incorporate any prior art. The scientific findings that provide the basis for this invention and which will be published in the two above-mentioned papers are 1) tumor growth is substantially inhibited in a host after the elevation of blood and plasma ATP levels, 2) administration of ATP and AMP into tumor-bearing hosts leads to elevated blood and plasma ATP levels, and 3) administration of AMP or ATP into tumor-bearing hosts, significantly inhibits the host weight loss which is an adverse result of cancer cachexia.

BEST AND VARIOUS MODES FOR CARRYING OUT INVENTION

Figure 1:
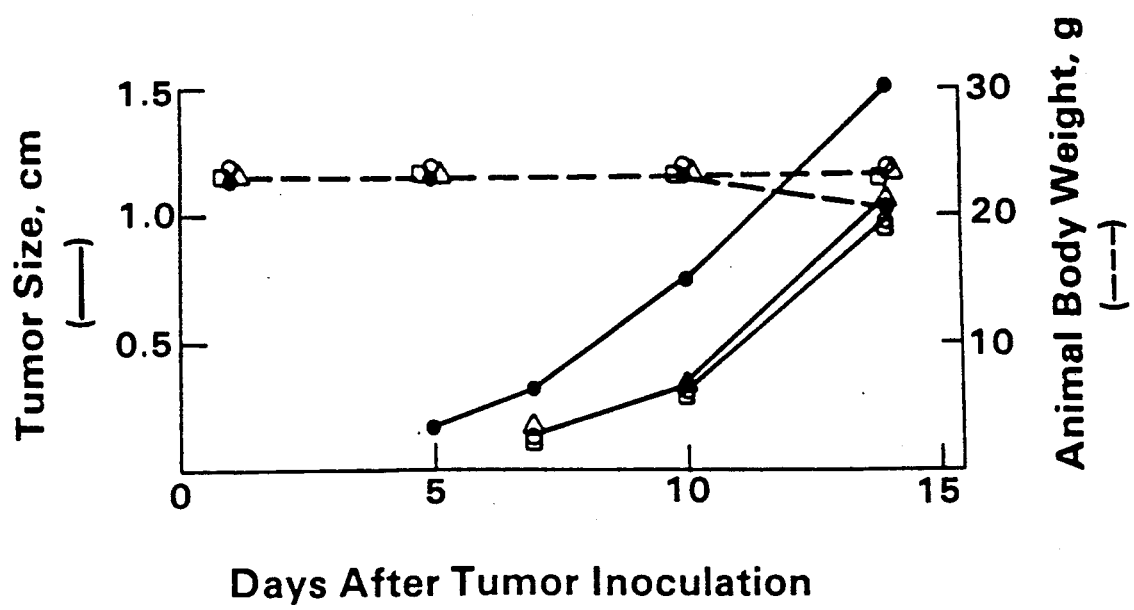
FIG. 1 illustrates the inhibition of growth of CT26 tumors in CB6F$_1$ mice and changes in host body weight during and after treatment with adenine nucleotides.

It has been found, pursuant to the present invention, that a host afflicted with a tumor where the affliction or disease has progressed to an advanced stage whereby there has been an adverse effect or profound alteration in host-tissue functions can be treated by increasing the blood and plasma ATP levels of the host to a level sufficient to thereby arrest the growth of the tumor cells and while substantially inhibiting weight loss caused by cachexia. Tumor as used herein refers to cancer cells such as malignant cells.

The blood and plasma ATP levels of the host can be increased by administering to the host adenosine 5'-monophosphate (AMP), and/or adenosine 5'-diphosphate (ADP), and/or adenosine 5'-triphosphate (ATP).

It has also been found in accordance with the present invention that a tumor-bearing host including a host wherein the progression of the disease is not to the extent discussed above can be treated by administering adenosine 5'-monophosphate (AMP) in an amount sufficient to increase the blood and plasma levels of adenosine 5'-triphosphate (ATP) in said host sufficiently to thereby arrest the growth of the tumor cells.

The use of AMP is preferred according to the present invention since it reduces the chances for adverse side-effects as compared to using ADP and ATP, especially since ATP is a known vasodilator. Non-limiting examples of tumor cells in a host that can be treated according to the present invention are CAPAN-1 and CT26.

The AMP and/or ADP and/or ATP treatment can be employed in a pharmaceutically acceptable salt form and can be employed in a variety of conventional pharmaceutical preparations. These preparations can contain organic or inorganic material suitable for internal administration. The high solubility of AMP and/or ADP and/or ATP salts in isotonic aqueous solutions of sodium chloride enable administration of these agents in the form of injection or infusion of single or multiple doses. The injection or infusion can be intraperitoneal, intravenous, or intra-arterial. AMP and/or ADP and/or ATP are also suitable for oral, enteral, or topical application when employed with conventional organic or inorganic carrier substances. The effective doses should be in the range of about 1–1,000 mg/kg of body weight for oral or topical administration and about 1–1,000 mg/kg of body weight for injections. Intravenous, intraperitoneal, or intraarterial infusions of AMP and/or ADP and/or ATP in a suitable salt form is preferably administered at a rate of about 0.001–15 mg/kg of body weight per minute.

The delivery of these agents can be performed using a variety of drug delivery systems including, but not limited to, pumps or liposomes. AMP or ADP or ATP can be employed not only as pharmaceutically acceptable salts, but as chelates to radio-nuclides such as, but not limited to, Tc-99m, In-111, or Ga-67. In this case, the AMP or ADP or ATP chelates of these agents can be employed for treatment as well as diagnosis of human tumors.

With regard to the rate of infusion of the AMP, and/or ADP, and/or ATP, the various references cited previously and disclosing that ATP is a known vasodilator, are noted. From these references it can be appreciated that single rapid injections of 40 mg of the sodium salt of ATP, either intravenously or intra-arterially, produced small subjective and physiological changes in human subjects. Slow injections or infusions of the same dose of ATP produced much lesser or no response at all (see Davies, et al., supra).

However, no such precautions are deemed necessary when employing AMP, as preferred by the present invention.

The following studies demonstrate the present invention in a non-limiting fashion. For example, adenosine 5'-triphosphate (ATP) and adenosine 5'-monophosphate (AMP) exhibit significant anticancer activities such as against established footpad CT26 colon adenocarcinoma in $CB6F_1$ mice. However, adenosine, inorganic phosphate, or inorganic pyrophosphate were without such effects under identical conditions.

Daily intraperitoneal (i.p.) injections of adenine nucleotides in large volumes of saline, starting after the tumors became palpable, resulted in inhibition of tumor growth and a few "cures". The treatment was not toxic to the host as determined by changes in body weights. Weight loss observed in animals upon progression of the fast-growing CT26 tumors was slowed markedly in adenine nucleotide-treated mice. The inhibition of weight loss in tumor-bearing mice was shown to be neither the cause nor the effect of the inhibition of tumor growth.

Intraperitoneal injections of AMP or ATP, but not of adenosine, yielded expansions of red blood cell (RBC) ATP pools in host animals. The expanded RBC ATP pools are stable over a period of hours while slowly releasing micromolar amount of ATP into the blood plasma compartment, leading to several fold increases in plasma (extracellular) ATP levels.

The tumor cell lines employed were CT26, a mouse undifferentiated, aggressive colon carcinoma, and CAPAN-1, a well-differentiated human pancreatic adenocarcinoma. These two tumors represent a broad spectrum of accepted tumor models and, therefore, are suitable for demonstrating the clinical efficacy of therapeutic agents for cancers in general not limited to the specific tumors tested. The cells are shown to be free of *Mycoplasma* contamination. Cells are cultured at 37° C. in a humidified atmosphere of 5% $CO_2$/95% air in MEM supplemented with antibiotics (100 units of penicillin per ml and 100 μg streptomycin per ml), L-glutamine (2 mM), non-essential amino acids (0.1 mM), sodium pyruvate (1 mM), and 10% fetal bovine serum.

In the tests, females and males $CB6F_1$ mice (a standard $F_1$ hybrid of BALB/C and C57BL/6) obtained from Jackson Laboratories, Bar Harbor, Maine and athymic outbred NCr nu/nu mice (males and females) from the Department of Radiation Medicine, Massachusetts General Hospital, Boston, Mass. 02114 are used. All the mice are kept for at least two weeks before inoculation of the tumors and the start of treatment and are 7–9 weeks old ($CB6F_1$) or 6–7 weeks old (athymic nu/nu) at the start of the procedure. Animals weigh 20–25 g (females) or 23–28 g (males), are housed 5–12 per cage, and have ad libitum access to food and water.

Tumor cells are removed from subconfluent cultures by a mild trypsin-EDTA treatment, the cell pellet is washed once with MEM without serum and the cells are suspended at the desired cell numbers in PBS (phosphate-buffered saline, 8 g NaCl, 0.2 g KCl, 1.15 g $Na_2HPO_4 \cdot 7H_2O$, and 0.2 g $KH_2PO_4$ per liter). Cell suspensions are shown to be at least 90% viable by trypan blue exclusion. Mice are injected subcutaneously in the right hind footpad with tumor cells suspended in 50 μl of PBS. The regular protocol (unless otherwise stated) consists of daily i.p. injections of 1 ml of 0.85% NaCl solution or 1 ml of 50 mM of AMP, ADP, or ATP in 0.85% NaCl (from stock solutions adjusted to pH 6.2) starting one day after tumor inoculation and given for ten consecutive days.

Injections are administered with 30 gauge needles and the mice are lightly anesthetized with ether. The mice are weighed before the start of treatment and once a week during and after treatment. After the tumors become palpable, tumor sizes are determined every three days. The animals are sacrificed, tumors are excised and weighed before they reach 10% of the animals' weight.

The blood (0.25 ml) is collected into syringes (25 gauge needles) containing citrate (0.05 ml of 93 mM sodium citrate, 7 mM citric acid, 140 mM dextrose, pH 6.5) from the inferior vena cava after i.p. injections of 1 ml of saline or 1 ml of 50 mM adenine nucleotides in saline. The mice are anesthetized with ether during the procedure. The plasma is prepared by immediate centrifugation of the blood in a Beckman microfuge (30 sec at 8000 xg). Blood (20 μl) or plasma (100 μl) aliquots are added to 1 ml of cold 7% trichloroacetic acid. Acid-soluble nucleotides are extracted for 30 minutes on ice and after removal of the precipitate by centrifugation, trichloroacetic acid is removed from the aqueous phase by vigorous extraction of the aqueous solution with 2 ml of 0.5 M tri-n-octylamine in Freon-113 (see Rapaport, "Compartmentalized ATP Pools Produced from Adenosine are Nuclear Pools", *J. Cell Physiol.*, 1980, 105, 267–274). The determination of ATP levels in the extracts is performed by bioluminometry (luciferin-luciferase) using a Turner Designs Bioluminescence Photometer. According to the procedure reported by Karl DM, Holm-Hansen O. "Effects of Luciferin Concentration on the Quantitative Assay of ATP Using Crude Luciferase Preparations", *Anal. Biochem.*, 1976, 75, 100–112.

The treatment of CB6F$_1$ mice and athymic nu/nu mice with daily i.p. injections of 1 ml of 50 mM of adenine nucleotides in saline (for 10 consecutive days) did not produce any weight losses during or after the treatment period, as illustrated by the results shown in FIG. 1.

FIG. 1 illustrates the inhibition of growth of CT26 tumors in CB6F$_1$ mice and changes in host body weights during and after treatment with adenine nucleotides. Tumor-bearing mice are treated with saline (•), AMP (o), ADP (Δ) or ATP (□) following procedures described above. FIG. 1 presents data from experiment number 4 of Table 1 hereinbelow. The values are the mean of 11 animals (per group). The standard deviations did not exceed 30% of the mean for any of the data points presented.

Occasionally, an animal treated with ATP or ADP would die a few hours after injection. However, healthy, non-stressed animals tolerate these doses and completely recover a few hours after treatment. Injections of AMP did not cause any deaths.

The growth inhibitory properties of adenine nucleotides against CT26 murine colon carcinoma, which are inoculated s.c. in the hind footpad of CB6F$_1$ mice, are illustrated in Table 1 hereinbelow. The efficacy of adenine nucleotides is demonstrated against high, intermediate and low tumor burdens. No significant differences between males and females are observed either in the rate of tumor growth or in the tumor's response to adenine nucleotides treatment.

TABLE 1

Effects of adenine nucleotides treatment on the growth of CT26 tumors in CB6F$_1$ mice.

| Experiment (No. of animals per group, sex) | Treatment[a] | No. of tumor cells inoculated | Time of analysis (days after inoculation) | Tumor diameter[b] cm | Tumor weight[c] g | Inhibition of tumor growth (% of saline-treated)[d] |
|---|---|---|---|---|---|---|
| 1 (10, F) | Saline | $0.5 \times 10^6$ | 15 | 1.8 ± 0.2 | 1.93 ± 0.23 | |
| | ATP-MgCl$_2$ | | | 1.4 ± 0.2 | 1.59 ± 0.24[g] | 18 |
| | ATP | | | 1.3 ± 0.2 | 1.34 ± 0.33[i] | 31 |
| 2 (10, M) | Saline | $0.5 \times 10^6$ | 15 | 1.9 ± 0.3 | 1.85 ± 0.37 | |
| | ATP-MgCl$_2$ | | | 1.4 ± 0.3 | 1.38 ± 0.40[f] | 26 |
| | ATP | | | 1.4 ± 0.2 | 1.30 ± 0.29[h] | 30 |
| 3 (12, M) | None | $0.5 \times 10^6$ | 13 | 1.6 ± 0.3 | 1.16 ± 0.20 | −1 |
| | Saline | | | 1.5 ± 0.3 | 1.14 ± 0.41 | |
| | AMP | | | 1.2 ± 0.2 | 0.65 ± 0.21[i] | 43 |
| | ADP | | | 1.3 ± 0.2 | 0.73 ± 0.23[g] | 36 |
| | ATP | | | 1.2 ± 0.2 | 0.70 ± 0.18[h] | 39 |
| 4 (11, F) | None | $0.5 \times 10^6$ | 14 | 1.6 ± 0.3 | 1.46 ± 0.25 | −7 |
| | Saline | | | 1.5 ± 0.3 | 1.36 ± 0.27 | |
| | AMP | | | 1.0 ± 0.3 | 0.88 ± 0.31[i] | 36 |
| | ADP | | | 1.1 ± 0.2 | 0.86 ± 0.27[i] | 37 |
| | ATP | | | 1.0 ± 0.2 | 0.84 ± 0.23[j] | 39 |
| 5 (12, F) | None | $0.5 \times 10^5$ | 16 | 1.1 ± 0.2 | 0.76 ± 0.16 | −7 |
| | Saline | | | 1.0 ± 0.2 | 0.71 ± 0.19 | |
| | AMP | | | 0.6 ± 0.2 | 0.41 ± 0.18[i] | 43 |
| | ATP | | | 0.5 ± 0.1 | 0.38 ± 0.10[j] | 47 |
| 6 (10, F) | Saline | $0.5 \times 10^5$ | 18 | 1.3 ± 0.2 | 0.94 ± 0.20 | |
| | AMP | | | 0.8 ± 0.2 | 0.56 ± 0.21[i] | 41 |
| | ATP | | | 0.8 ± 0.1 | 0.51 ± 0.18[j] | 46 |
| | AP$_4$A[k] | | | 0.9 ± 0.3 | 0.74 ± 0.21[e] | 22 |
| 7 (10, F) | Saline | $0.1 \times 10^5$ | 22 | 1.5 ± 0.3 | 1.19 ± 0.26 | |
| | AMP | | | 0.9 ± 0.5 | 0.51 ± 0.28[j, l] | 57 |

TABLE 1-continued

Effects of adenine nucleotides treatment on the growth of CT26 tumors in CB6F$_1$ mice.

| Experiment (No. of animals per group, sex) | Treatment[a] | No. of tumor cells inoculated | Time of analysis (days after inoculation) | Tumor diameter[b] cm | Tumor weight[c] g | Inhibition of tumor growth (% of saline-treated)[d] |
|---|---|---|---|---|---|---|
| | ATP | | | 0.9 ± 0.5 | 0.68 ± 0.36[h, l] | 43 |

[a]Treatment was performed as described above. In experiments 1 and 2, animals were treated with 1 ml of 25 mM of ATP-MgCl$_2$ or 1 ml of 25 mM of ATP. In experiments 3-7, animals were treated with 1 ml of 50 mM of AMP, ADP, or ATP.
[b]Tumor diameter was calculated from L + W/2. Mean ± S.D.
[c]The weight of footpad tumors immediately after excision. Mean ± S.D.
[d]Inhibition was based on tumor weights.
[e-j]Statistically significant differences from saline-treated group by Student's t test.
[e]$P < 0.1$.
[f]$P < 0.05$.
[g]$P < 0.025$.
[h]$P < 0.01$.
[i]$P < 0.005$.
[j]$P < 0.001$.
[k]Ap$_4$A, a nucleotide that is degraded to ATP and AMP by ecto-enzymatic phosphodiesterases was injected at a concentration of 10 mM.
[l]Included one complete cure.

Table 2, below, demonstrates the effects of adenine nucleotides on the arrest of CT26 tumors in CB6F$_1$ mice and of CAPAN-1 xenografts in athymic nude mice,.

TABLE 2

Arrest of growth of CT26 tumors in CB6F$_1$ mice and CAPAN-1 xenografts in athymic nu/nu mice by adenine nucleotides treatment.

| Experiment (Host, No. of animals per group, sex) | Treatment[a] | No. of tumor cells inoculated | Time of analysis (Weeks after inoculation) | Arrested tumors/ implanted tumors |
|---|---|---|---|---|
| 1 (CB6F$_1$, 10, F) | Saline | 0.5 × 10$^4$ | 5 | 0/10 |
| | AMP | | | 2/10[b] |
| | ATP | | | 4/10[d] |
| 2 (Athymic, nu/nu 5, F) | Saline | 1 × 10$^5$ | 7 | 1/5 |
| | ATP | | | 4/5 |
| 3 (Athymic, nu/nu 5, F) | Saline | 1 × 10$^5$ | 6 | 1/5 |
| | ATP | | | 3/5 |
| 4 (Athymic, nu/nu 11, F) | Saline | 0.5 × 10$^5$ | 10 | 3/11 |
| | AMP | | | 7/11[c] |
| | ATP | | | 8/11[d] |
| 5 (Athymic, nu/nu 10, F) | Saline | 0.5 × 10$^5$ | 9 | 2/10 |
| | AMP | | | 6/10[c] |
| | ADP | | | 6/10[c] |
| | ATP | | | 8/10[e] |

[a]Treatment was performed as described above. Intraperitoneal injection is of 1 ml of saline or 1 ml of 50 mM of adenine nucleotides were administered.
[b-e]Differences between these groups and the saline treated groups of the same experiment are significant by the $\chi^2$ test.
[b]$P < 0.5$.
[c]$P < 0.25$.
[d]$P < 0.1$.
[e]$P < 0.05$.

The data reported in Table 1 and Table 2 suggest that the efficacy of adenine nucleotides in inhibiting the growth of CT26 tumors is increased when the inoculated tumor burden is intermediate or low. When 10$^4$ or 5×10$^3$ tumor cells are implanted, treatment with adenine nucleotides resulted in a few "cures". "Cured" mice are kept alive for 4 months without appearance of a tumor.

Concentrations of AMP and ATP which are lower than 50 mM are as effective against CT26 footpad tumors in CB6F$_1$ mice when administered by daily intraperitoneal injections in volumes of 1.4-1.8 ml of saline. The start of the treatment schedule can be delayed until the tumors are palpable (6-10 days after tumor inoculation, depending on the number of tumor cells implanted) without any significant effects on the magnitude of tumor growth inhibition. The efficacy of the inhibition of tumor growth is also dependent to a small extent on the pH of the AMP and ATP solutions which are administered i.p., with pHs 5.5-6.2 being the most effective.

The effects of AMP, ADP, and ATP on human tumor xenografts in nude mice were evaluated utilizing the pancreatic ductal adenocarcinoma CAPAN-1 (see Kyriazis AP, Kyriazis AA, Scarpelli DG, Fogh J, Rao SM, Lepera R., "Human Pancreatic Adenocarcinoma Line CAPAN-1 in Tissue Culture and the Nude Mouse", *Am. J. Pathol.*, 1982, 106, 250-260).

Treatment schedules consist of single daily i.p. injections for 10 consecutive days, starting one day after tumor inoculation. Tumor burden is relatively low (0.5-1×10$^5$ cells implanted) and tumor growth is slow (tumors became palpable 4-6 weeks after inoculation). The effects of AMP, ADP, and ATP are evaluated by the total arrest of tumor growth for a period of 6-10 weeks (lack of palpable footpad tumors) and in all cases the tumor-free mice do not develop any tumors for a period of 4 months. The data presented in Table 2 demonstrate the effects of adenine nucleotides on the arrest of CAPAN-1 xenografts in athymic nude mice.

In order to demonstrate that intraperitoneally-introduced adenine nucleotides can elevate blood and plasma ATP levels after entry into the systemic circulation, blood samples are withdrawn from the inferior vena cava at several time points after the i.p. injections. The data reported in Table 3 below show that administration of AMP, ADP, and ATP yield elevated blood and plasma ATP levels and that total cellular, as well as extracellular ATP concentrations in the circulation remain higher than its levels in normal controls for a period of several hours.

The data outlined in Table 3 indicate that the magnitude of the increases in plasma ATP concentrations is linked to the increases in blood (total cellular) ATP concentrations. The increase in total blood ATP levels after i.p. injections of AMP or ATP last for more than 5 hours and less than 18 hours, at which point total blood ATP pools drop back to normal levels. All the expanded ATP pools are accounted for in red blood cells and are stable after extensive washing of the isolated red blood cells in Hanks' balanced salt solution. Slow release of ATP from red blood cells containing expanded ATP pools are responsible for the increases in the plasma ATP levels.

The use of citrate-dextrose as an anticoagulant as compared to heparin, yields higher levels of plasma ATP pools (data for heparin is not shown). Citrate, but not heparin, was shown recently to inhibit the activity of a blood plasma phosphodiesterase, which is active in catalyzing the degradation of ATP, by chelating divalent cations required for the enzymatic activity (see Luthje J. Ogilvie A., "Catabolism of Ap$_3$A and Ap$_4$A in Human Plasma. Purification and Characterization of Glycoprotein Complex with 5'-Nucleotide Phosphodiesterase Activity", *Eur. J. Biochem.*, 1985, 149, 119-127). Inhibition of this phosphodiesterase activity during the short period of plasma preparation is presumably responsible for the higher plasma ATP levels obtained by utilizing this anticoagulant.

TABLE 3

ATP levels in mouse blood (total cellular) and plasma after i.p. injections of adenine nucleotides.

| Host | Treatment[a] | Blood ATP levels[b] (hours after treatment) mM | Plasma ATP levels[b] (hours after treatment) μM |
|---|---|---|---|
| CB6F$_1$ | Saline | 0.65 ± 0.16 (1) | 0.87 ± 0.25 (1) |
|  |  | 0.69 ± 0.15 (5) | 0.94 ± 0.21 (5) |
| CB6F$_1$ | AMP | 1.23 ± 0.21 (1) | 1.75 ± 0.36 (1) |
|  |  | 1.36 ± 0.24 (5) | 1.69 ± 0.19 (5) |
| CB6F$_1$ | ADP | 1.28 ± 0.30 (1) | 2.66 ± 0.46 (1) |
|  |  | 1.65 ± 0.41 (5) | 2.75 ± 0.87 (5) |
| CB6F$_1$ | ATP | 2.53 ± 0.61 (1) | 3.99 ± 0.81 (1) |
|  |  | 3.47 ± 0.57 (5) | 5.14 ± 0.71 (5) |
| Athymic nu/nu | Saline | 0.83 ± 0.25 (1) | 1.10 ± 0.36 (1) |
|  |  | 0.91 ± 0.37 (4) | 0.99 ± 0.43 (4) |
| Athymic nu/nu | AMP | 1.87 ± 0.46 (1) | 2.17 ± 0.36 (1) |
|  |  | 2.35 ± 0.67 (4) | 1.97 ± 0.41 (4) |
| Athymic nu/nu | ATP | 2.71 ± 0.54 (1) | 2.93 ± 0.69 (1) |
|  |  | 4.26 ± 0.79 (4) | 3.01 ± 0.76 (4) |

[a]Each mouse (7-9 week old females) received i.p. injections of 1 ml of saline or 1 ml of 50 mM AMP, ADP, or ATP in saline and the procedures performed as described above.
[b]Each group consisted of three mice and data are expressed as mean ± S.D. Blood withdrawal was performed within 15 minutes of the 1 hour time points and within 30 minutes of the 4 and 5 hour time points. The corresponding blood and plasma ATP levels were determined on the same blood samples in all cases.

A further series of tests are conducted whereby tumors are inoculated by injections of $2.5 \times 10^5$ CT26 cells (over 90% viability) in 50 μl of phosphate-buffered saline into the right hind footpad of CB6F$_1$ mice. The treatments were initiated at a variety of times after inoculation of the tumors. The injection schedules started either 1 or 5 days after tumor inoculation when none of the tumors are palpable or when the tumors are clearly palpable (average calculated weight of 100 mg), which occur in 100% of the inoculated mice after 8-11 days. Mice are randomized, divided into groups, and injected daily with 2.2 ml of saline, adenosine, AMP, or ATP (compounds are in sterile saline solutions at concentrations of 25 mM with AMP and ATP solutions adjusted to pH 6.2). Injections are administered intraperitoneally with 30 gauge needles and the mice are lightly anesthetized with either. The mice are weighed and tumor sizes measured before the start of the treatment schedule and every three days during and after the treatment schedule. These determinations are performed before injections during the treatment period.

The blood (0.25 ml) is collected into 1 ml syringes (26 gauge needles) containing either citrate-dextrose (0.05 ml of 93 mM sodium citrate, 7 mM citric acid, 140 mM dextrose, pH 6.5) or sodium heparin (0.05 ml of 3 units of sodium heparin in saline) from the inferior vena cava. The mice are anesthetized with ether during the procedure. Plasma or Hanks' (Balanced Salt Solution) BSS media from incubated isolated RBCs (Red Blood Cells) are prepared by centrifugation of whole blood or RBCs in a Beckman microfuge (30 seconds at 8000 xg) and samples of 100 μl are added to 1 ml of ice-cold 7% trichloroacetic acid. Red blood cells are prepared by centrifugation of whole blood (1500 xg for 5 minutes at 4° C.) and removal of plasma and the buffy coat is followed by a wash of the pelleted RBCs (from 250 μl of whole blood) in 5 ml of ice-cold Hanks' BSS. After centrifugations, the RBCs pellet is resuspended in Hanks' BSS to yield a total volume with the original hematocrit (percent of RBCs volume in the whole blood). Aliquots of 20 μl of RBCs suspensions or whole blood are added to 1 ml of ice-cold 7% trichloroacetic acid. Extraction of acid-soluble nucleotides and determinations of ATP levels by luminometry followed procedures discussed hereinabove. Levels of [$^3$H]ATP in whole blood, RBCs, plasma, or RBCs incubation media (Hanks' BSS) are determined after incorporation of 250 μCi of [$^3$H]adenosine of specific radioactivity of 30 Ci/mmol (1 Ci=$3.7 \times 10^{10}$ becquerels) into whole blood or RBC suspensions (250 μl total) followed by immediate trichloroacetic acid extractions as described above. Two dimensional thin layer chromatography on poly(ethylene)imine cellulose with an unlabeled ATP carrier is performed according to Bochner and Ames, *J. Biol. Chem.*, 257, pp. 9759-9769, 1982). For the determination of whole blood or isolated RBC [$^3$H]ATP pools, 10 μl of a 1 ml initial trichloroacetic acid extract are chromatographed. Determinations of [$^3$H]ATP levels in blood plasma or RBCs incubation media are performed on 300 μl of an initial 1 ml trichloroacetic acid extract which are lyophilized and redissolved in 15 μl of water. After chromatography, the spots corresponding to the ATP carrier are cut, eluted with 0.5 ml of 4 N ammonium hydroxide, and radioactivity determined in 10 ml of scintillation fluid.

Figure 2:
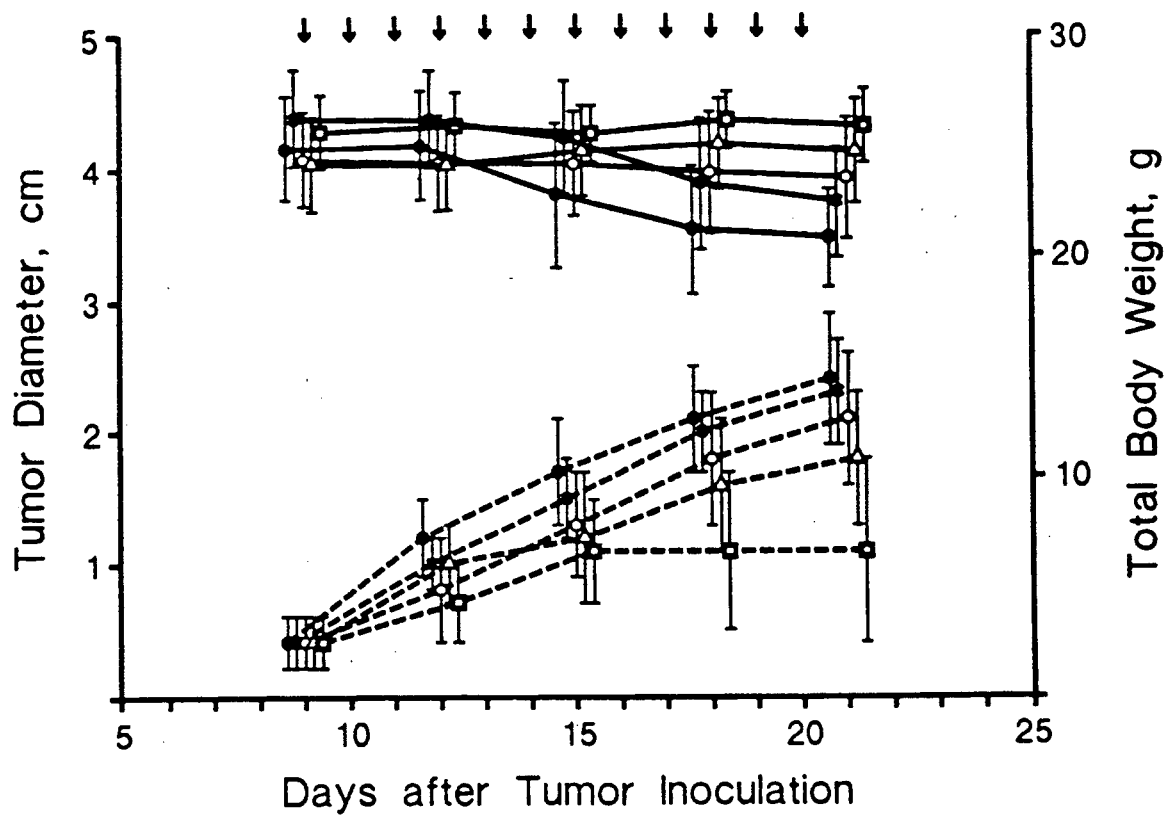
FIG. 2 illustrates inhibition of tumor growth and host weight loss in tumor-bearing mice by treatment with adenine nucleotides.

The therapeutic efficacy of adenine nucleotides is demonstrated against footpad murine CT26 colon adenocarcinoma grown in CB6F$_1$ mice. In particular, see FIG. 2. FIG. 2 illustrates inhibition of tumor growth (---) and host weight loss (—) in tumor-bearing mice by treatment with adenine nucleotides. Mice (CB6F$_1$, 8 week old males) bearing palpable CT26 footpad tumors (on day 9 after tumor inoculation) are treated with saline (●), adenosine (o), AMP (Δ), or ATP (□) as described herein. An untreated group is also included (x). Arrows indicate days of injection. This representative experiment included 10 animals per treatment group and data points are expressed as the means ± S.D. No deaths occurred before day 22 after tumor inoculation.

Daily i.p. administration of AMP and of ATP in 2.2 ml of saline (at pH 6.2) for 12 days starting after the tumors become palpable, significantly inhibit the growth of this fast-growing tumor. Much weaker anticancer activities are exhibited by equimolar amounts of adenosine (see FIG. 2) whereas equimolar amounts of either inorganic phosphate or inorganic pyrophosphate in saline at pH 6.2 are without any effects on the growth of CT26 tumors in CB6F$_1$ mice under identical conditions. The magnitude of the antitumor activities of AMP and ATP depends to a small extent on the pH of the solution administered intraperitoneally. This property is probably related to the number of negative charges on the phosphate groups (the pKa of the secondary phosphate is around 6.6). AMP and especially ATP have some buffering capacity, and at a pH below 6.6 they carry a smaller net charge than at a physiological pH. The lower charge of these molecules enhances the initial (first hour) transport of AMP and ATP across the peritoneal membrane and into the systemic circulation (see Torres, et al., 1978, *Pharmacol.*, 17, 330–340). No inhibition of tumor growth is exhibited when either AMP or ATP were administered by the same 12 consecutive days schedule, ending one day before tumor inoculation. The treatment schedule of palpable CT26 tumors which is illustrated in FIG. 2 consistently yields 10–20% of "cures". These mice remain tumor-free for at least two months. When applied to palpable tumors, inhibition of tumor growth by ATP is more pronounced than that obtained with AMP (FIG. 2). AMP, however, is as effective as ATP in inhibiting tumor growth in the same model system when the treatment schedule is initiated one day after tumor inoculation.

Figure 3:
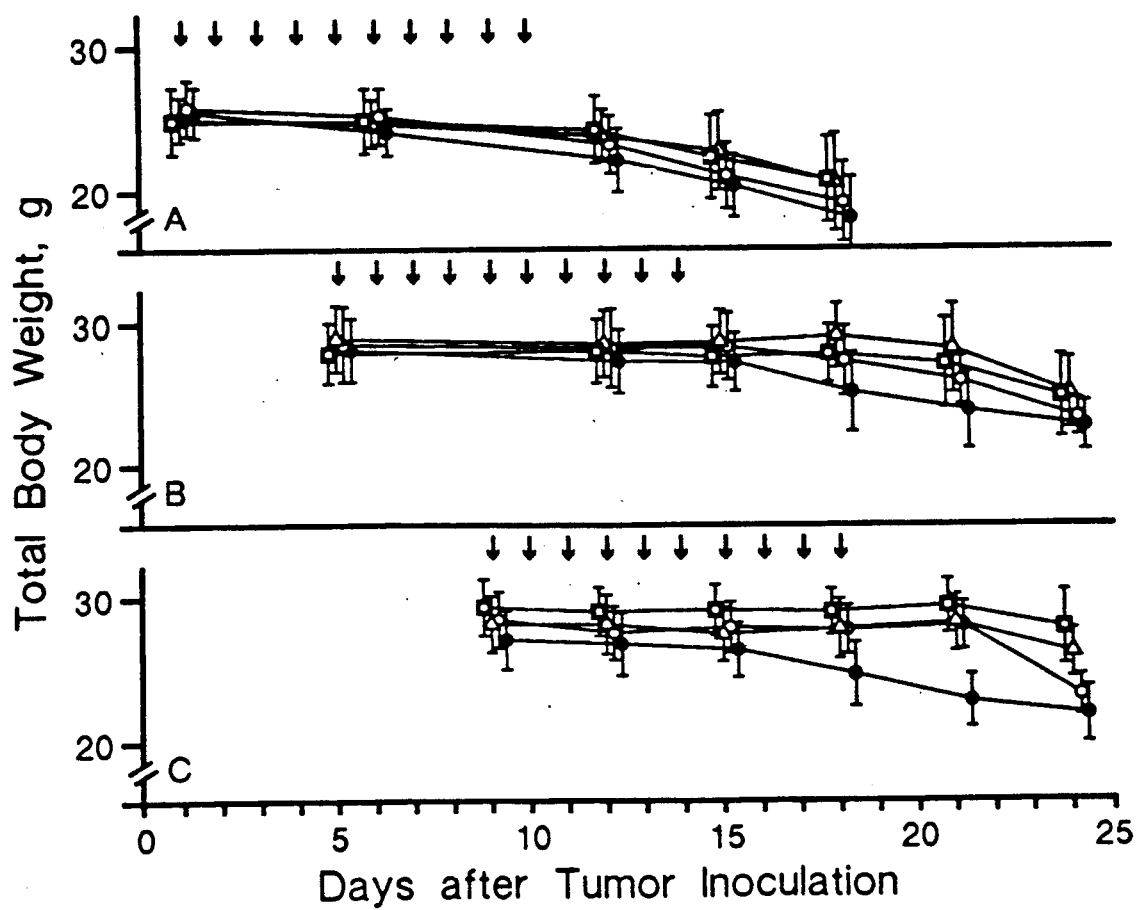
FIG. 3 illustrates inhibition of host weight loss in tumor-bearing animals by treatment with adenine nucleotides.

FIG. 3 further illustrates inhibition of host weight loss in tumor-bearing animals by treatment with adenine nucleotides. Mice (CB6F$_1$, males, 7 weeks old, in A, 10 weeks old in B, C) are inoculated with CT26 tumors and daily treatments (for 10 consecutive days) with saline (○), adenosine (o), AMP (Δ), or ATP (□) are initiated 1 day (A), 5 days (B), or 9 days after tumor inoculation (when all the tumors were palpable) (C). Arrows indicate days of injection. Experimental procedures were outlined in the text. Each treatment group included 10 animals and data points are expressed as means ± S.D. No deaths occurred before day 19 (A) or day 25 (B,C).

When treatment schedules end long before the tumors become relatively large, the inhibition of the rate of weight loss can be correlated with the inhibition of tumor growth where adenosine is having only a small effect on either of the two phenomena (FIGS. 3A and 3B). When adenine nucleotides are administered only after the tumors became palpable, the CT26 tumors turned progressively larger during the treatment schedule (FIGS. 2 and 3C). In this case, the inhibition of tumor growth can be separated from the inhibition of weight loss. Comparing tumors of similar sizes, the data in FIG. 2 indicate that adenosine, and to a somewhat larger extent, AMP and ATP inhibit weight loss in a manner that can be dissociated from their inhibitory effects on tumor sizes. Another way of demonstrating the same phenomenon is by using a variety of treatment schedules where one is completed before weight losses occur (FIG. 3A), while another treatment schedule is completed at the time when weight losses are beginning to be observed (FIG. 3B), and the third treatment schedule is applied during the period of weight losses in tumor-bearing mice (FIG. 3C). It is established herein that the largest inhibition of animal weight loss occurs when a 10-day daily injection schedule is initiated on day 9 after inoculation of the tumors when they are palpable (FIG. 3C). Starting the same injection schedule earlier on day 1 or day 5 after tumor inoculation yielded lower levels of inhibition of weight loss (day 5) or inhibition of weight loss which is only the result of the smaller tumors in the treated animals (day 1) (FIGS. 3A and 3B).

The expansion of RBC ATP pools after intraperitoneal injections and the slow release of ATP from RBCs are illustrated in Table 4 below.

Single intraperitoneal injections of 2 ml of 35 mM of AMP or ATP in saline at pH 6.2 into CB6F$_1$ mice result in expansions of RBC ATP pools in these mice (see Table 4).

TABLE 4

| Expansion of RBC ATP pools and blood plasma ATP levels 5 hours after intraperitoneal injections of AMP and ATP into mice* | | | |
|---|---|---|---|
| Compound administered | RBC ATP pools⁻ mM | Plasma ATP levels⁺ μM | Plasma [³]ATP levels immediately after [³H]adenosine incorporation into whole blood μM |
| Saline | 0.81 ± 0.14 | 0.74 ± 0.14 | 0.56 ± 0.22 |
| Adenosine | 1.10 ± 0.24 | 1.12 ± 0.28 | 0.77 ± 0.30 |
| AMP | 1.78 ± 0.32 | 3.10 ± 0.96 | 2.86 ± 1.06 |
| ATP | 2.49 ± 0.42 | 4.94 ± 1.17 | 5.75 ± 2.05 |

*Blood was withdrawn into a syringe containing citrate-dextrose as an anticoagulant. [³H]Adenosine was taken up by whole blood for 10 seconds and half of the blood sample was immediately spun-down for plasma isolation. The other half was used for the isolation of washed RBCs which were resuspended in a volume of Hanks' BSS to yield the original hematocrit before the removal of an aliquot for ATP determination. Plasma [³]ATP levels were calculated from the radioactivity of plasma [³H]ATP after correlation with the specific radioactivity of RBC [³H]ATP pools which, in turn, were determined by bioluminometry and two-dimensional thin layer chromatography. Data represent the means ± S.D. of three separate experiments.
⁻Determined by bioluminometry.

The expansions of RBC ATP pools after i.p. injections of AMP or ATP could be detected 30 minutes after injections and lasted for approximately 6–8 hours after the nucleotides were completely adsorbed across the peritoneal membrane and into the systemic circulation. The rates of adsorption of intraperitoneal AMP or ATP solutions varied in different strains of mice. The increases in RBC ATP pools are comparable to the increases observed in total blood ATP levels after similar i.p. injections of AMP or ATP as illustrated above in Table 3. Adenosine, at levels similar to those of AMP or ATP, is only slightly effective in expanding mouse RBC ATP pools (Table 4). Plasma (extracellular) ATP levels are markedly increased after i.p. administration of AMP or ATP. These plasma ATP levels originate in RBCs since they can be metabolically labeled by [³H]adenosine. Plasma ATP pools which originate in the dense granules of blood platelets would not be radioactively labeled under the same conditions (e.g., Holmsen, 1985, Seminars in Hematol, 22, 219–240). The experiments described in Tables 4 and 5 include uptake of

[³H]adenosine by whole blood (Table 4) or isolated washed RBCs (Table 5 below). In both cases, all the extracellular ATP, determined seconds after the uptake of [³H]adenosine, is metabolically labeled.

TABLE 5

Stability of expanded RBC ATP pools after intraperitoneal injections of AMP and ATP into mice*

| Compound administered | RBC ATP pools+ mM (37° C.) (min) 0 | RBC ATP pools+ mM (37° C.) (min) 120 | ATP levels in the medium+ (Hanks' BSS) μM | Medium (Hanks' BSS) [³H]ATP levels immediately after [³H]adenosine incorporation into isolated, washed RBCs (at time 0) μM |
|---|---|---|---|---|
| Saline | 0.68 | 0.56 | 1.10 | 1.09 |
| Adenosine | 0.69 | 0.54 | 1.71 | 1.20 |
| AMP | 1.01 | 0.86 | 2.42 | 1.81 |
| ATP | 2.52 | 1.76 | 4.08 | 4.93 |

*Blood was withdrawn into a syringe containing citrate-dextrose. Plasma and buffy coat were removed after centrifugation and RBCs were washed with 5 ml of Hanks' BSS. RBCs were resuspended in a volume of Hanks' BSS to yield the original hematocrit and [³H]adenosine was taken up by the cells for 10 seconds. An aliquot of the total cell suspension was fixed in 1 ml of trichloroacetic acid and the remaining RBCs suspension was used for the determination of the 120 minute time point or was centrifuged for the isolation of the medium. ATP levels in the media were determined at time 0. Determinations of [³H]ATP levels in the Hanks' BSS incubation media were identical to determinations performed in blood plasma and which were described in the footnote to Table 4. Data represent the average of two separate experiments.
+ Determined by bioluminometry.

The radioactively labeled [³H]ATP in blood plasma (Table 4) or in the media in which the washed RBCs are suspended (Table 5) show good correlations with the actual ATP levels which are determined by bioluminometry. Therefore, it is concluded that the origin of plasma ATP levels are in the RBC ATP pools. The findings that the ratios of plasma or medium ATP levels to the cellular (RBC) ATP pools increase when RBC ATP pools are expanded suggest that the release of ATP from RBCs into the extracellular compartment is a specific process that is probably not related to hemolysis of RBCs. An equal degree of hemolysis of RBCs during the 40 seconds (10 seconds of labeling and 30 seconds of centrifugation) that elapse from the time of uptake of [³H]adenosine to the time of isolation and fixation of the extracellular media, would have lead to similar ratios of extracellular to RBC ATP levels for all forms of treatment. Mice injected with AMP or ATP show not only expanded RBC ATP pools, as compared to saline- or adenosine-treated mice, but higher plasma ATP levels relative to their (expanded) RBC ATP pools (Table 4).

The stability of the expanded RBC ATP pools in vitro was also demonstrated. Two hour incubations of washed isolated RBCs containing normal or expanded ATP pools in Hanks' BSS result in relatively small decreases in RBC ATP pools with the expanded pools being maintained well above normal levels (Table 5). The expansions of RBC ATP pools after i.p. administration of AMP or ATP in vivo is presumably the result of their dephosphorylation followed by the RBCs uptake of the adenosine which is generated in situ. The in vitro treatment of whole mouse blood with AMP or ATP resulted in marginal increases in RBC ATP pools (see Table 6 below).

TABLE 6

Rates of degradation of 1 mM ATP by mouse or human blood in vitro in the presence of heparin or citrate as anticoagulants. Lack of expansion of RBC ATP pools under the same conditions.*

| Added nucleotide (1 mM) | Rate of extracellular ATP degradation mouse blood pmol/μl · min citrate | Rate of extracellular ATP degradation mouse blood pmol/μl · min heparin | Rate of extracellular ATP degradation human blood pmol/μl · min citrate | Rate of extracellular ATP degradation human blood pmol/μl · min heparin | RBC ATP pools⁻ (after 30 min incubations in heparinized mouse blood) μM |
|---|---|---|---|---|---|
| ATP | 6.87 | 10.21 | 1.75 | 4.07 | 0.76 ± 0.05 |
| AMP | | | | | 0.73 ± 0.10 |
| Adenosine | | | | | 0.55 ± 0.17 |
| Saline | | | | | 0.67 ± 0.10 |

*Blood (450 μl) was withdrawn into a syringe containing either 50 μl of citrate-dextrose or 50 μl of heparin (100 U/ml). Whole blood was then added to 1 mM of [³H]ATP in saline (25 μl) and at various time points blood aliquots (90 μl) were removed and centrifuged. Plasma (20 μl) was withdrawn and added to 1 ml of ice-cold trichloroacetic acid. Thin layer chromatography on poly(ethyleneimine cellulose was performed according to published procedures. The rate of degradation of 1 mM of [³H]ATP was linear for mouse or human blood during the initial 30 minute incubation at 37° C.
⁻ RBC ATP pools were determined in isolated washed RBCs after incubations of whole blood with 1 mM of the specified compound by bioluminometry. Data represent means ± S.D. of three separate experiments.

The in vitro degradation of ATP proceeds faster in heparinized blood as compared to citrated blood, reaffirming the role of plasma phosphodiesterase(s) in catalyzing this catabolic reaction (see Luthje, 1985, *Eur. J. Biochem.*, 149, 119–127). Citrate has been shown to chelate metal cations required for this activity (see Luthje, supra). It is thus concluded that the in vivo generation of adenosine by the in situ dephosphorylation of AMP or ATP requires ecto-enzymatic activities which are present in the vascular bed. It is important to note that the degradation of ATP by human blood in vitro proceeds at a slower rate than the degradation of ATP by mouse blood under identical conditions (Table 6).

Normal levels of ATP in human plasma are submicromolar, such as about 0.1–0.5 || M. The elevated levels for the purposes of the present invention need only be one order of magnitude higher, such as about 1 to about 5 μM.

The data discussed above lead to the following conclusions:
1. Adenine nucleotides can be utilized to expand the total cellular ATP pools (steady state levels) of pathologically normal RBCs and that these RBCs slowly release their expanded ATP pools into the extracellular blood plasma compartment.

2. The ratio of extracellular ATP to total RBC ATP pools increases in the following order of treatment, saline<adenosine<AMP<ATP (Table 4); and, therefore, the release of RBC ATP pools is likely to originate in mechanism(s) other than (or in addition to) hemolysis, which would yield similar ratios of extracellular ATP levels to total RBC ATP pools for all treatment groups.

3. Endothelial cells or blood platelets are not the in vivo source of extracellular blood plasma ATP in the data reported above. The in vivo source of elevated blood plasma (extracellular) ATP levels are RBCs.

4. Adenine nucleotide treatments are useful to achieve significant tumor-growth-inhibitory activity as demonstrated by the results achieved after daily i.p. injections of either AMP or ATP starting at a point when the aggressive fast-growing CT26 tumor were palpable in syngeneic mice. The demonstration of the substantial inhibition of tumor growth after administration of AMP or ATP to tumor-bearing hosts was performed in murine (mouse) models in a nonlimiting fashion. This model is commonly used in the evaluation of therapeutic efficacy and host toxicity of cancer chemotherapeutic agents.

5. The clinical utility of anticancer treatment with adenine nucleotides is enhanced by their demonstrated inhibition of host weight loss in tumor-bearing animals when the tumors become progressively larger. At this point, the effects of cancer cachexia are manifested in the host. The administration of AMP or ATP to cachectic hosts affords a treatment which inhibits both the tumor growth and the adverse effects of cachexia on host body mass by processes which do not bear a cause-effect relationship.

6. The utilization of AMP for the treatments of tumor-bearing hosts may be preferable to the use of ATP for the same purposes because AMP produces less side-effects than ATP in these host animals.

Having thus described my invention, what I claim as new and desire to secure by Letters Patent is:

1. A process for selectively arresting the growth of tumor cells in a host which comprises administering to a host having tumor cells adenosine 5'-monophosphate, or pharmaceutically acceptable salts thereof, or chelates thereof or liposomes thereof, or radio-nuclides thereof in an amount sufficient to increase the blood and plasma levels of adenosine 5'-triphosphate in said host sufficiently to thereby arrest the growth of said tumor cells.

2. The process of claim 1 wherein said amount is a low dose of about 0.1 to about 1,000 mg/kg of body weight and said administering is oral or topical.

3. The process of claim 1 wherein said amount is a low dose of about 1–100 mg/kg of body weight and said administering is by injection.

4. The process of claim 1 wherein said delivery is accomplished by infusion at a rate of 0.001–15 mg/kg of body weight of said host per minute.

5. The process of claim 1 wherein adenosine 5'-monophosphate is administered.

6. The process according to claim 1 wherein said tumor cells are human tumor cells.

7. The process according to claim 6 wherein said human tumor cells are a solid tumor.

8. A process for selectively arresting the growth of tumor cells in a host and while substantially inhibiting weight loss caused by cancer cachexia in said host which comprises treating a host afflicted with a tumor to the extent that host tissues or organ functions are adversely effected to increase the blood and plasma levels of adenosine 5'-triphosphate in said host to a level sufficient to thereby arrest the growth of said tumor cells and while substantially inhibiting weight loss caused by cancer cachexia.

9. The process of claim 8 wherein said treating is with at least one compound selected from the group of adenosine 5'-monophosphate, adenosine 5'-diphosphate, adenosine 5'-triphosphate, pharmaceutically acceptable salts thereof, chelates thereof, liposomes thereof and radio-nuclides thereof.

10. The process of claim 8 wherein said treating is with adenosine 5'-monophosphate or pharmaceutically acceptable salts thereof, or chelates thereof, or liposomes thereof radio-nuclides thereof.

11. The process of claim 8 wherein said treating is with adenosine 5'-monophosphate.

12. The process of claim 8 wherein said treating is with adenosine 5'-triphosphate, or pharmaceutically acceptable salts thereof, or chelates thereof, or liposomes thereof radio-nuclides thereof.

13. The process of claim 8 wherein said treating is with adenosine 5'-triphosphate.

14. The process of claim 8 wherein said amount is a low dose of about 1 to about 1,000 mg/kg of body weight and said administering is oral or topical.

15. The process of claim 8 wherein said amount is a low dose of about 1–1,000 mg/kg of body weight and said administering is by injection.

16. The process of claim 8 wherein said delivering is accomplished by infusion at a rate of 0.001–15 mg/kg of body weight of said host per minute.

17. The process of claim 8 wherein said host is a human host.

18. A process for treatment of tumors in a host which comprises treating a tumor-bearing host to increase the blood and plasma levels of adenosine 5'-triphosphate in said host to a level sufficient for said treatment.

19. The process of claim 18 wherein said treating is with adenosine 5'-monophosphate or pharmaceutically acceptable salts thereof, or chelates thereof liposomes thereof, or radio-nuclides thereof.

20. The process of claim 19 wherein said amount is a low dose of about 1 to about 1000 mg/kg of body weight and said administering is oral or topical.

21. The process of claim 18 wherein said amount is a low dose of about 1 to about 1000 mg/kg of body weight and said administering is oral or topical.

22. The process of claim 18 wherein said amount is a low dose of about 1–100 mg/kg of body weight and said administering is by injection.

23. The process of claim 19 wherein said amount is a low dose of about 1–100 mg/kg of body weight and said administering is by injection.

24. The process of claim 18 wherein adenosine 5'-monophosphate is administered.

25. The process of claim 18 wherein said tumor is a human tumor.

26. The process of claim 18 wherein said host is a human host.

27. The process of claim 18 wherein said administering is accomplished by infusion of a rate of 0.001–15 mg/kg of body weight of said host per minute.

28. The process of claim 19 wherein said administering is accomplished by infusion at a rate of 0.001–15 mg/kg of body weight of said host per minute.

29. A process for increasing the blood and plasma levels of adenosine 5'-triphosphate in a host which comprises administering at least one compound selected from the group of adenosine 5'-monophosphate, adenosine 5'-diphosphate, adenosine 5'-triphosphate, pharmaceutically acceptable salts thereof, chelates thereof liposomes thereof, and radio-nuclides thereof to said host in an amount sufficient to increase said blood and plasma levels.

30. The process of claim 29 wherein said amount is a low dose of about 1 to about 100 mg/kg of body weight and said administering is oral or topical.

31. The process of claim 29 wherein said amount is a low dose of about 1–100 mg/kg of body weight and said administering is by injection.

32. The process of claim 29 wherein said administering is accomplished by infusion at a rate of 0.001–15 mg/kg of body weight of said host per minute.

33. The process of claim 29 wherein adenosine 5'-monophosphate or adenosine 5'-triphosphate is administered.

34. The process of claim 29 wherein at least one compound from the group of adenosine 5'-triphosphate pharmaceutically acceptable salts thereof, chelates thereof, liposomes thereof and radio-nuclides is administered.

35. The process of claim 29 wherein adenosine 5'-triphosphate is administered.

36. The process according to claim 29 wherein said host is a human host.

37. The process of claim 29 wherein at least one compound from the group of adenosine 5'-monophosphate, pharmaceutically acceptable salts thereof, chelates thereof, liposomes thereof and radio-nuclides is administered.

38. The process of claim 29 wherein adenosine 5'-monophosphate is administered.

39. The process of claim 29 wherein said delivering is accomplished by infusion at a rate of 0.001–1.5 mg/kg of body weight of said host per minute.

40. The process of claim 29 wherein the administering is oral.

41. The process of claim 40 wherein said amount is a low dose of about 1 to about 10 mg/kg of body weight.

42. The process of claim 29 wherein the administering is topical.

43. The process of claim 42 wherein said amount is a low dose of about 1 to about 10 mg/kg of body weight.

44. The process of claim 29 wherein the administering is by injection.

45. The process of claim 44 wherein said amount is a low dose of about 1 to 10 mg/kg of body weight.

* * * * *